United States Patent
Cornacchia

(10) Patent No.: US 7,117,971 B1
(45) Date of Patent: Oct. 10, 2006

(54) STETHOSCOPE COVER APPLICATOR

(76) Inventor: Damian J. Cornacchia, 11 Woodsview Dr., Boothwyn, PA (US) 19061

( * ) Notice: Subject to any disclaimer, the term of this patent is extended or adjusted under 35 U.S.C. 154(b) by 0 days.

(21) Appl. No.: 11/241,362

(22) Filed: Oct. 3, 2005

(51) Int. Cl.
*A61B 7/02* (2006.01)

(52) U.S. Cl. .................. 181/131; 181/137; 221/266

(58) Field of Classification Search ............ None
See application file for complete search history.

(56) References Cited

U.S. PATENT DOCUMENTS

| | | | |
|---|---|---|---|
| 3,930,697 A | 1/1976 | Barouh et al. | |
| 4,871,046 A * | 10/1989 | Turner | 181/131 |
| 4,884,734 A | 12/1989 | Kahl, Jr. et al. | |
| 5,424,495 A * | 6/1995 | Wurzburger | 181/131 |
| D361,089 S | 8/1995 | Teng | |
| 5,448,025 A * | 9/1995 | Stark et al. | 181/131 |
| 5,466,897 A * | 11/1995 | Ross et al. | 181/131 |
| 5,528,004 A * | 6/1996 | Wurzburger | 181/131 |
| D375,162 S | 10/1996 | Gilbert | |
| 5,686,706 A | 11/1997 | Wurzburger | |
| 5,747,751 A | 5/1998 | Weckerle et al. | |
| 5,808,244 A * | 9/1998 | Knight et al. | 181/131 |
| 5,878,932 A * | 3/1999 | Huang | 225/65 |
| 6,009,971 A | 1/2000 | Weidman et al. | |
| 6,019,187 A | 2/2000 | Appavu | |
| 6,041,889 A * | 3/2000 | Stark et al. | 181/131 |
| D430,213 S * | 8/2000 | Huang | D19/69 |
| 6,112,659 A * | 9/2000 | Huang | 101/226 |
| 6,206,134 B1 | 3/2001 | Stark et al. | |
| 6,467,568 B1 * | 10/2002 | Kemper | 181/131 |
| 6,499,560 B1 * | 12/2002 | Lang et al. | 181/131 |
| 6,971,527 B1 * | 12/2005 | Chandaria | 211/13.1 |

* cited by examiner

*Primary Examiner*—Jeffrey Donels
*Assistant Examiner*—Eduardo Colon Santana

(57) ABSTRACT

A stethoscope cover applicator for facilitating application of a protective membrane to the stethoscope includes a membrane member configured to be selectively secured to a diaphragm of the stethoscope to inhibit contact between the skin of the patient and the stethoscope. An axle is couplable to the membrane member and the membrane member is rolled around the axle. A base member configured to engage a support surface receives the axle to facilitate unrolling of the membrane member from the axle.

13 Claims, 4 Drawing Sheets

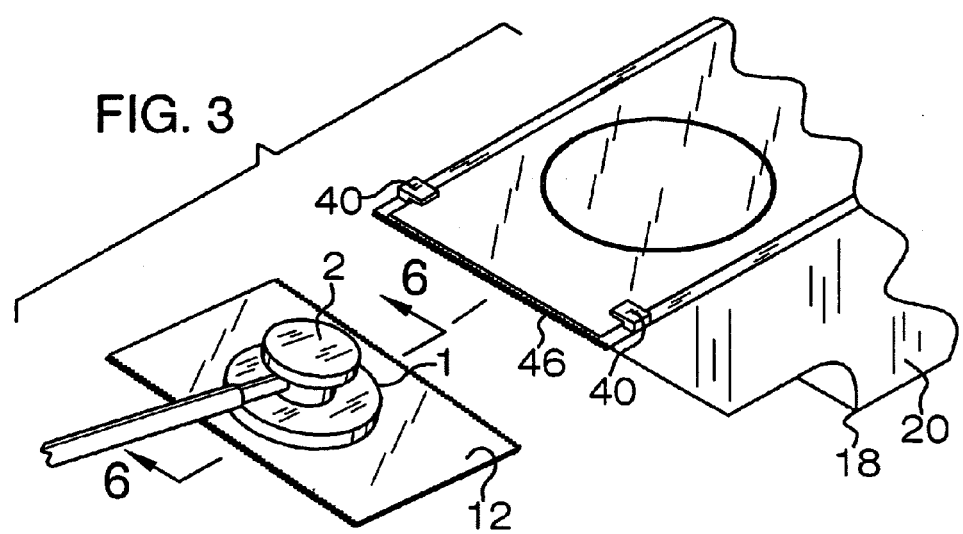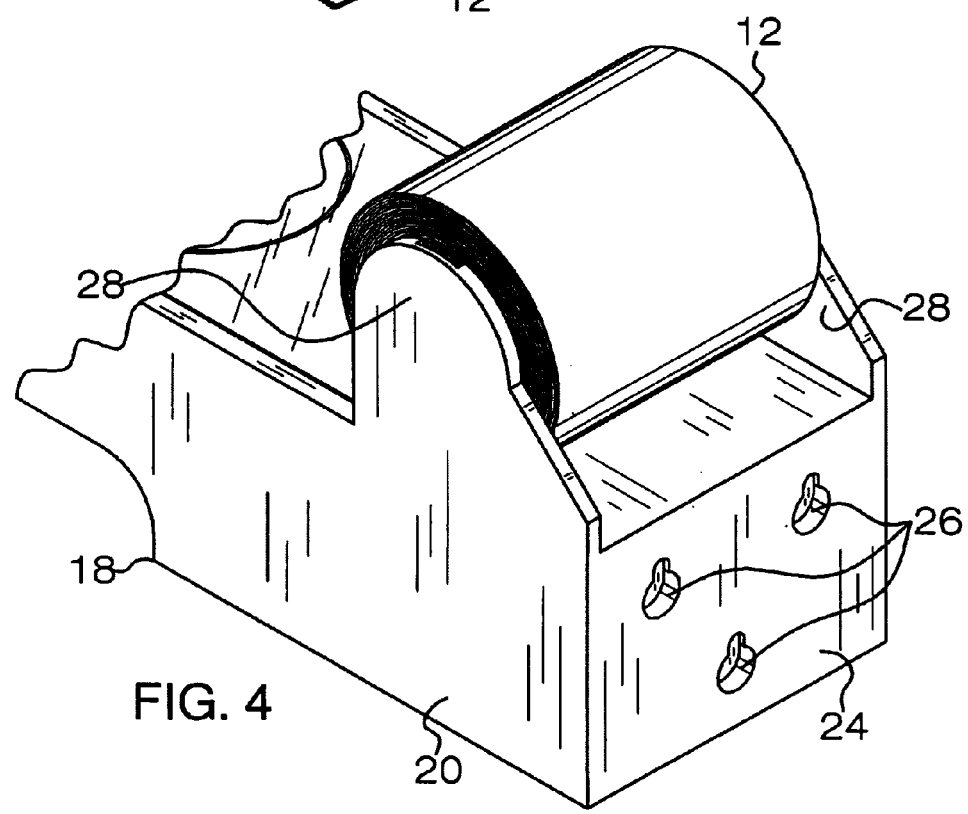

STETHOSCOPE COVER APPLICATOR

BACKGROUND OF THE INVENTION

1. Field of the Invention

The present invention relates to disposable stethoscope shields and more particularly pertains to a new disposable stethoscope shield for facilitating application of a protective membrane to the stethoscope.

2. Description of the Prior Art

The use of disposable stethoscope shields is known in the prior art. U.S. Pat. No. 6,009,971 describes a device for applying a plurality of shields to a stethoscope and allowing one shield to be peeled away after each use to prevent disease transmission between patients. Another type of disposable stethoscope shield is U.S. Pat. No. 6,019,187 for providing a diaphragm for the stethoscope that can be readily removed and discarded and replaced with a new diaphragm.

While these devices fulfill their respective, particular objectives and requirements, the need remains for a device that has certain improved features allowing for the protective membrane to be applied easily with minimal contact between the doctor and the protective membrane. Such a membrane is preferably positionable on stethoscopes to not only prevent contamination between patients but also allows for less heat transfer between the patient and the stethoscope so that the stethoscope feels relatively less cold to the patient.

SUMMARY OF THE INVENTION

The present invention meets the needs presented above by generally comprising a membrane member configured to be selectively secured to a diaphragm of the stethoscope to inhibit contact between the skin of the patient and the stethoscope. An axle is couplable to the membrane member to allow the membrane member to be rolled around the axle. A base member is configured to engage a support surface. The base member receives the axle to facilitate unrolling of the membrane member from the axle.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a an enlarged perspective view of the present invention showing a portion of the membrane member separated from the rest of the membrane member.

FIG. 4 is an enlarged perspective view of the rear wall of the present invention.

DESCRIPTION OF THE PREFERRED EMBODIMENT

Figure 1:
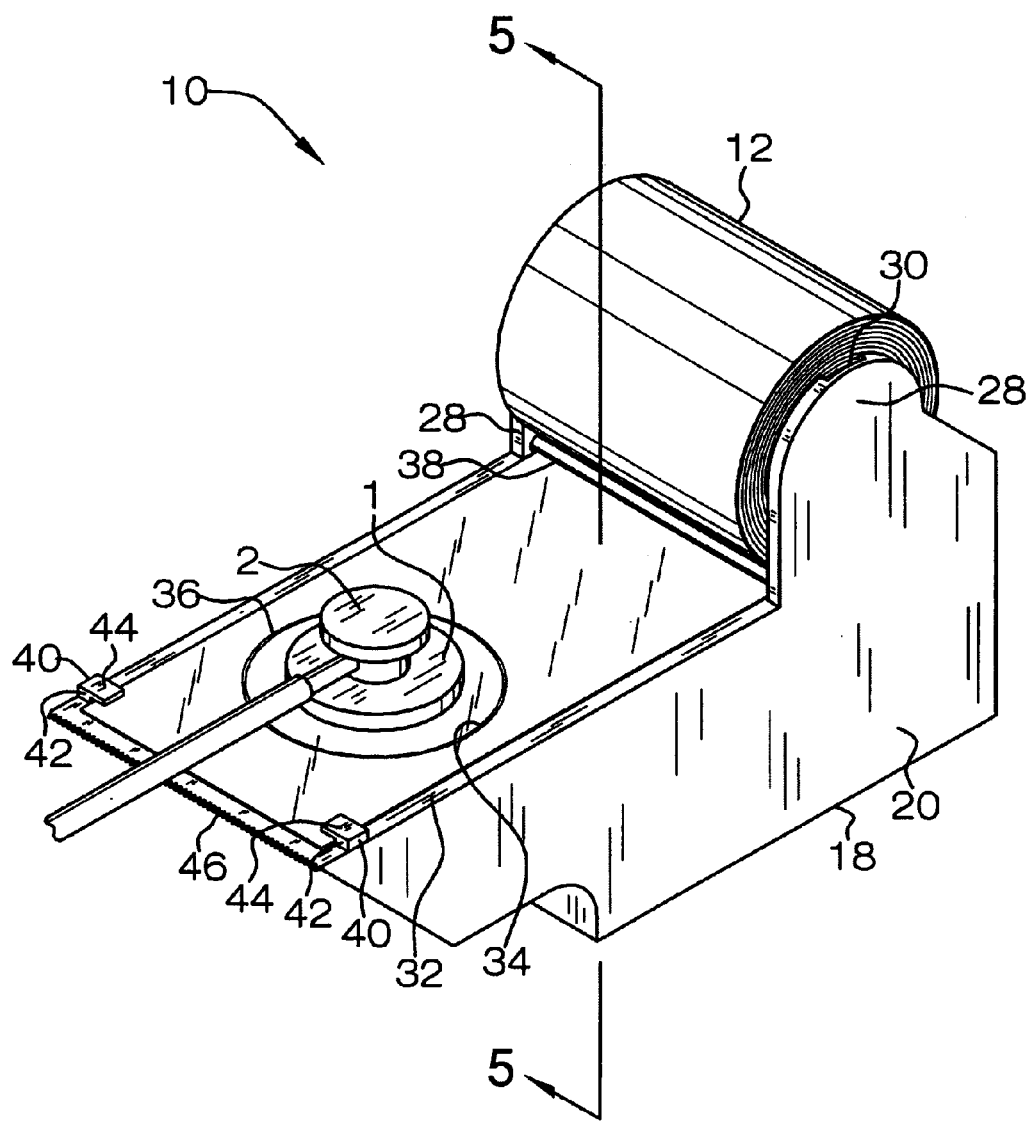
FIG. 1 is a perspective view of a stethoscope cover applicator according to the present invention.
Figure 2:
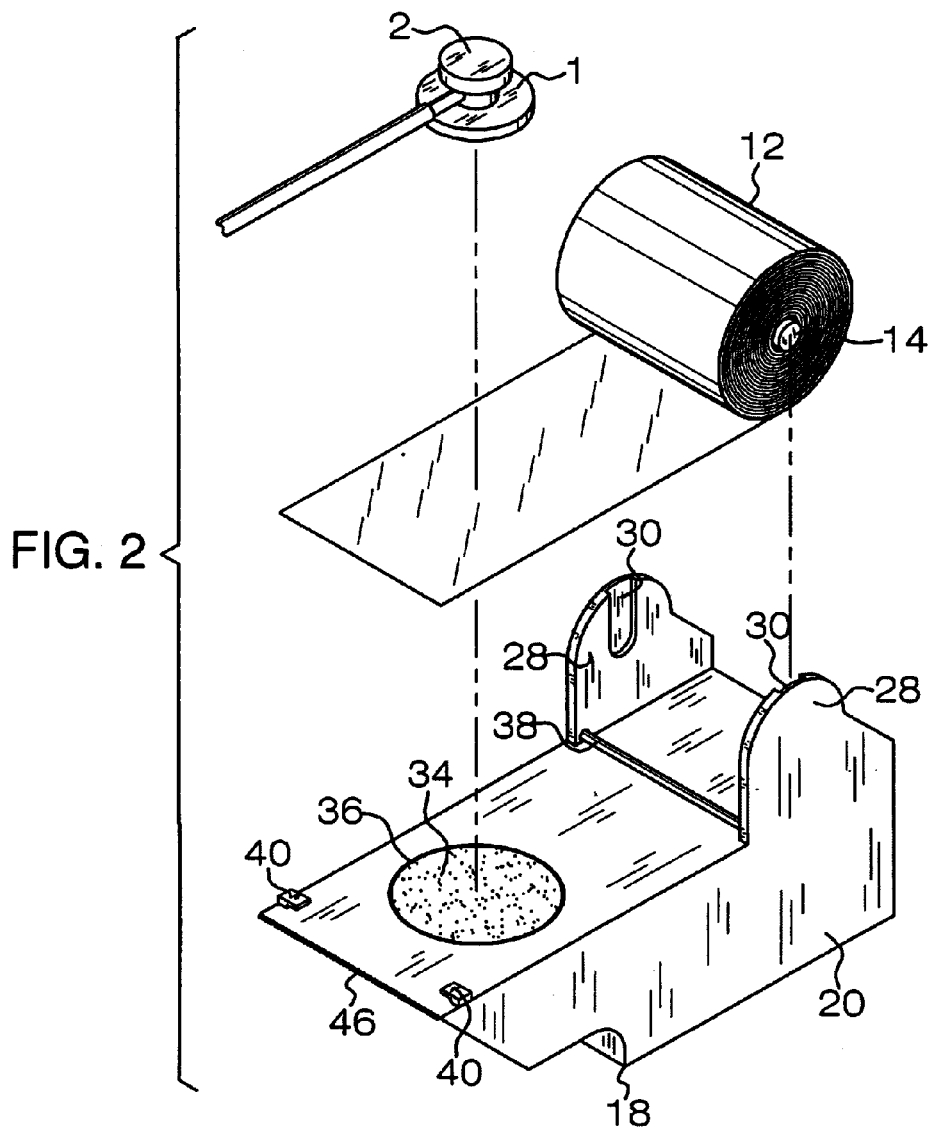
FIG. 2 is an exploded perspective view of the present invention.
Figure 5:
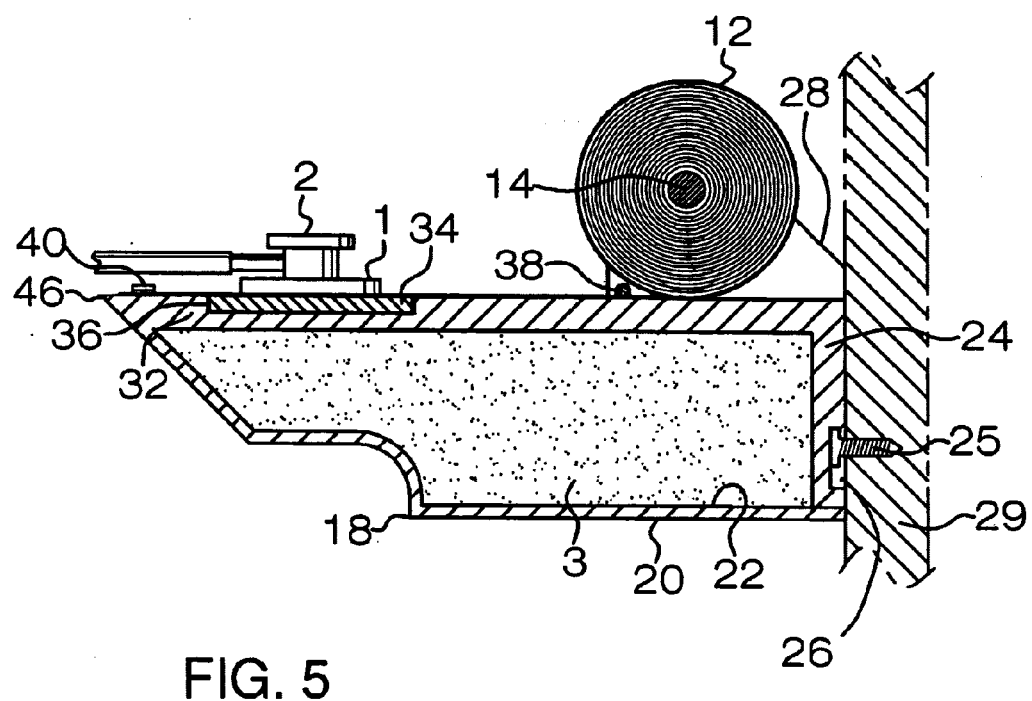
FIG. 5 is a cross-sectional view of the present invention taken along line 5—5 of FIG. 1.
Figure 6:
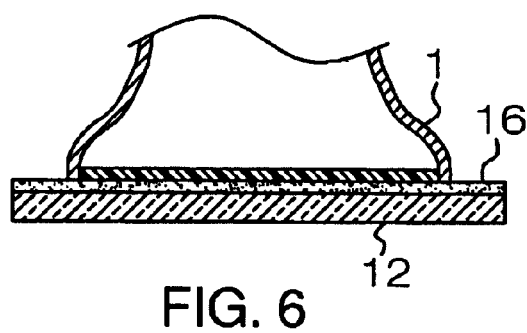
FIG. 6 is a partial cross-sectional view of the present invention taken along line 6—6 of FIG. 3.

With reference now to the drawings, and in particular to FIGS. 1 through 6 thereof, a new disposable stethoscope shield embodying the principles and concepts of the present invention and generally designated by the reference numeral 10 will be described.

As best illustrated in FIGS. 1 through 6, the stethoscope 2 cover applicator 10 generally comprises a membrane member 12 configured to be selectively secured to a diaphragm 1 of a stethoscope 2 to inhibit contact between the skin of the patient and the stethoscope 2. An axle 14 is couplable to the membrane member 12 to allow the membrane member 12 to be rolled onto and off of the axle 14. The membrane member 12 may include any conventional plastic film that is preferably flexible and has a thickness of less than 0.10 cm.

An adhesive 16 coupled to one side of the membrane member 12 to permit releasable adhesion of the membrane member 12 to the diaphragm 1 of the stethoscope 2. The adhesive 16 may be any conventional pressure sensitive adhesive configured to be completely and easily removed from the diaphragm 1 to inhibit any residue from the adhesive 16 remaining on the stethoscope 2 when the membrane member 12 is removed from the stethoscope 2.

A base member 18 is configured to engage a support surface. The base member 18 receives the axle 14 to facilitate unrolling of the membrane member 12 from the axle 14. The base member 18 includes a perimeter wall 20 defining an interior space 22 to receive sand 3, or other weighting material such as a solid weight or water, to weight the base member 18 and inhibit sliding of the base member 18 across a horizontal support surface. The perimeter wall 20 may further include a rear wall 24 having a plurality of keyhole slots 26 configured to selectively receive fasteners 25 extended into a vertical support surface 29 to allow the base member 18 to be suspended from the vertical support surface. The base member 18 includes a pair of stanchions 28 extending upwardly from the perimeter wall 20. Each of the stanchions 28 is positioned proximate the rear wall 24. Each of the stanchions 28 includes a channel 30 configured to receive the axle 14 to allow the axle 14 to extend between the stanchions 28. The axle 14 rotates in the channel 30 of each of the stanchions 28 to allow the membrane member 12 to be unrolled from the axle 14 along a deck wall 32 of the perimeter wall 20 so that the adhesive 16 is positioned upwardly and opposite the deck wall 32.

The base member 18 may further include a pad member 34 positioned in a depression 36 extending into the deck wall 32. The pad member 34 is positioned under the membrane member 12 when the membrane member 12 extends along the deck wall 32. The pad member 34 cushions the diaphragm 1 of the stethoscope 2 when the stethoscope 2 is pressed onto the membrane member 12 to adhere the stethoscope 2 to the membrane member 12.

The base member 18 may also include a spindle 38 extending between the stanchions 28 and being positioned above the deck wall 32 to allow the membrane member 12 to be unrolled from the axle 14 substantially parallel to the deck wall 32. The spindle 38 rotates to allow the spindle 38 to roll along the membrane member 12 and inhibit the spindle 38 binding the membrane member 12 when the membrane member 12 is unrolled from the axle 14.

A pair of guides 40 is coupled to the deck wall 32 of the perimeter wall 20. The guides 40 extend over the deck wall 32. The membrane member 12 passes between the guides 40 and the deck wall 32. Each of the guides 40 includes a riser portion 42 and an extension portion 44. The riser portion 42 of each of the guides 40 extends upwardly from the deck wall 32 and the extension portion 44 of the associated one of the guides 40 extends back over the deck wall 32 a spaced distance from the deck wall 32 and toward each other. The membrane member 12 is allowed to pass between the extension portion 44 of each of the guides 40 and the deck wall 32. The guides 40 maintain alignment of the membrane member 12 along the deck wall 32. The guides 40 are positioned on opposite sides of the deck wall 32 to permit the stethoscope 2 to pass between the guides 40 when the stethoscope 2 is adhered to the membrane member 12.

The base member 18 further includes a cutting edge 46 coupled to the perimeter wall 20 opposite the rear wall 24 and aligned with the deck wall 32. The cutting edge 46 is configured to separate a portion of the membrane member 12 when the membrane member 12 is forced down on the cutting edge 46.

In use, the user presses the diaphragm 1 of the stethoscope 2 onto the membrane member 12 and down onto the pad member 34 to secure the adhesive 16 of the membrane member 12 to the stethoscope 2. The stethoscope 2 is then pulled away from the stanchions 28 and between the guides 40 and unrolling the membrane member 12 from the axle 14. Once the stethoscope 2 is beyond the cutting edge 46 the user presses down with the stethoscope 2 to force the membrane down over the cutting edge 46 and separate the membrane member 12 adhered to the stethoscope 2 from the rest of the membrane member 12. The user can then use the stethoscope 2 on a patient's skin and then remove the membrane member 12 from the stethoscope 2 to inhibit cross contamination between patients.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A stethoscope cover applicator for limiting an amount of direct contact that a patient has with a diaphragm of a stethoscope, said stethoscope cover applicator comprising:
   a membrane member configured to be selectively secured to the diaphragm of the stethoscope to inhibit contact between the skin of the patient and the stethoscope;
   an axle being couplable to said membrane member to allow said membrane member to be rolled around said axle; and
   a base member configured to engage a support surface, said base member receiving said axle to facilitate unrolling of said membrane member from said axle, said base member including a perimeter wall defining an interior space, a pad member being positioned in a depression extending into a deck wall of said perimeter wall, said pad member being positioned under said membrane member when said membrane member extends along said deck wall, said pad member cushioning the diaphragm of the stethoscope when the stethoscope is pressed onto said membrane member to adhere the stethoscope to the membrane member.

2. The stethoscope cover applicator as set forth in claim 1, further including an adhesive coupled to one side of said membrane member, said adhesive permitting releasable adhesion of said membrane member to the diaphragm of the stethoscope.

3. The stethoscope cover applicator as set forth in claim 1, wherein said base member further includes a rear wall having a plurality of keyhole slots configured to receive fasteners and allowing said base member to be suspended from a vertical support surface.

4. The stethoscope cover applicator as set forth in claim 1, further including sand being positioned in said interior space to weight said base member and inhibit sliding of said base member across a horizontal support surface.

5. The stethoscope cover applicator as set forth in claim 4, wherein said base member includes a cutting edge coupled to said perimeter wall, said cutting edge being configured to separate a portion of said membrane member when said membrane member is forced down on said cutting edge.

6. The stethoscope cover applicator as set forth in claim 1, wherein said perimeter wall further includes a rear wall having a plurality of keyhole slots configured to receive fasteners and allowing said base member to be suspended from a vertical support surface.

7. The stethoscope cover applicator as set forth in claim 1, wherein said base member includes a pair of stanchions extending upwardly from said perimeter wall, each of said stanchions configured to receive said axle to allow said axle, said axle extending between said stanchions, wherein said membrane member may be unrolled from said axle.

8. The stethoscope cover applicator as set forth in claim 7, wherein each of said stanchions includes a channel configured to receive said axle, said axle extending between said stanchions said axle rotating in said channel of each of said stanchions to allow said membrane member to be unrolled from said axle along a deck wall of said perimeter wall so that said adhesive is positioned upwardly and opposite said deck wall.

9. The stethoscope cover applicator as set forth in claim 7, wherein said base member includes a spindle rotatably coupled to and extending between said stanchions to allow said spindle to roll along said membrane member, said membrane member extending from said axle and under said spindle.

10. The stethoscope cover applicator as set forth in claim 1, wherein said base member includes a pair of guides coupled to said perimeter wall, each of said guides extending over said perimeter wall to permit said membrane member to pass between said guides and said perimeter wall to maintain alignment of said membrane member along said perimeter wall.

11. The stethoscope cover applicator as set forth in claim 10, wherein each of said guides includes a riser portion and an extension portion, each of said riser portions of said guides extending upwardly from said perimeter wall, each of said extension portions extending over said perimeter wall a spaced distance from said perimeter wall to allow said membrane member to pass between said extension portion of each of said guides and said perimeter wall to maintain alignment of said membrane member along said deck wall, said guides being positioned on opposite sides of said perimeter wall to permit the stethoscope to pass between said guides when the stethoscope is adhered to said membrane member.

12. The stethoscope cover applicator as set forth in claim 11, wherein said base member includes a cutting edge coupled to said perimeter wall, said cutting edge being configured to separate a portion of said membrane member when said membrane member is forced down on said cutting edge.

13. A stethoscope cover applicator for limiting an amount of direct contact that a patient has with a diaphragm of a stethoscope, said stethoscope cover applicator comprising:

a membrane member configured to be selectively secured to the diaphragm of the stethoscope to inhibit contact between the skin of the patient and the stethoscope;

an adhesive coupled to one side of said membrane member, said adhesive permitting releasable adhesion of said membrane member to the diaphragm of the stethoscope;

an axle being couplable to said membrane member to allow said membrane member to be rolled onto and off of said axle;

a base member being configured to engage a support surface, said base member receiving said axle to facilitate unrolling of said membrane member from said axle, said base member including;

a perimeter wall defining an interior space, sand being positioned in said interior space to weight said base member, said perimeter wall including a rear wall having a plurality of keyhole slots configured to receive fasteners to allow said base member to be suspended from a vertical support surface;

a pair of stanchions extending upwardly from said perimeter wall, each of said stanchions being positioned proximate said rear wall, each of said stanchions including a channel configured to receive said axle to allow said axle to extend between said stanchions, said axle rotating in said channel of each of said stanchions to allow said membrane member to be unrolled from said axle along a deck wall of said perimeter wall so that said adhesive is positioned upwardly and opposite said deck wall;

a pad member being positioned in a depression extending into said deck wall, said pad member being positioned under said membrane member when said membrane member extends along said deck wall, said pad member being configured to cushion the diaphragm of the stethoscope when the stethoscope is pressed onto said membrane;

a spindle extending between and being rotatably coupled to said stanchions, said spindle being positioned above said deck wall, said membrane member being unrolled from said axle and being extendable under said spindle such that said membrane is substantially parallel to said deck wall;

a pair of guides, each of said guides being coupled to said deck wall of said perimeter wall, said guides extending over said deck wall, said membrane member passing between said guides and said deck wall, each of said guides including a riser portion and an extension portion, each of said riser portions upwardly from said deck wall, each of said extension portions extending back over said deck wall a spaced distance from said deck wall, said membrane member passing between said extension portion of each of said guides and said deck wall to maintain alignment of said membrane member along said deck wall, said guides being positioned on opposite sides of said deck wall to permit the stethoscope to pass between said guides when the stethoscope is adhered to said membrane member; and a cutting edge coupled to said perimeter wall opposite said rear wall and aligned with said deck wall, said cutting edge being configured to separate a portion of said membrane member when said membrane member is forced down on said cutting edge.

* * * * *